United States Patent [19]

Brooks

[11] Patent Number: 4,969,466
[45] Date of Patent: Nov. 13, 1990

[54] INFLATION RATE CONTROL CIRCUIT FOR BLOOD PRESSURE CUFFS

[75] Inventor: James R. Brooks, Portland, Oreg.

[73] Assignee: Spacelabs, Inc., Redmond, Wash.

[21] Appl. No.: 244,985

[22] Filed: Sep. 15, 1988

[51] Int. Cl.⁵ ............................................. A61B 5/02
[52] U.S. Cl. .................................. 120/681; 128/680; 128/682; 128/677; 128/679
[58] Field of Search .................... 128/672, 677–686; 137/565; 364/415–417; 417/312, 540–544

[56] References Cited

U.S. PATENT DOCUMENTS

| | | | |
|---|---|---|---|
| 4,178,918 | 12/1979 | Cornwell | 128/682 |
| 4,252,127 | 2/1981 | Gemelke | 128/680 |
| 4,378,807 | 4/1983 | Peterson et al. | 128/680 X |
| 4,493,326 | 1/1985 | Hill et al. | 128/680 |
| 4,510,940 | 4/1985 | Wesseling | 128/681 X |
| 4,567,899 | 2/1986 | Kamens et al. | 128/680 |
| 4,832,039 | 5/1989 | Perry et al. | 128/682 X |

FOREIGN PATENT DOCUMENTS 0078090 10/1982 European Pat. Off. .
3424535A1 9/1986 Fed. Rep. of Germany .
2071399A 9/1981 United Kingdom .

*Primary Examiner*—Max Hindenburg
*Assistant Examiner*—Robin R. Longo
*Attorney, Agent, or Firm*—Seed and Berry

[57] ABSTRACT

A blood pressure monitor having a motor driven air pump for inflating an blood pressure cuff, and a control system for controlling the voltage applied to the motor to regulate the rate at which the cuff is inflated. The control system utilizes a microprocessor to calculate a desired inflation rate and then compare the desired inflation rate with the actual inflation rate to generate a control signal in the form of a pulse-width modulated square wave. The square wave is low-pass filtered to generate a voltage reference that is applied to one input of a comparator. The other input of the comparator receives a feedback signal indicative of the voltage applied to the motor. The comparator generates a sqaure wave having a duty cycle that is a determined by the polarity of the comparison at its inputs. The square wave modulates a semi-conductor switch which, in turn, controls the voltage applied to the motor.

10 Claims, 2 Drawing Sheets

INFLATION RATE CONTROL CIRCUIT FOR BLOOD PRESSURE CUFFS

DESCRIPTION

1. Field of the Invention

This invention relates to blood pressure measuring instruments, and, more particularly, to a circuit for controlling the motor of an air pump to inflate a blood pressure cuff at a controlled rate.

2. Background of the Invention

Medical diagnostic procedures increasingly are becoming automated through the use of electronic instruments that mimic the actions of trained medical personnel. As a result, diagnostic procedures can be performed without the need for trained personnel, thus making ambulatory and bedside monitoring of various physiological parameters practical.

One example of an instrument for automatically performing medical diagnostic tests is the ambulatory or bedside blood pressure monitor. These blood pressure monitors include a conventional blood pressure cuff connected through a tube to a monitoring instrument. The monitoring instrument includes an electric motor driving an air pump, a pressure transducer for measuring the air pressure in the cuff, and, if a separate transducer is not used, to also detect Korotkoff sounds or oscillometric pulses. All of these components are generally controlled by a microprocessor. The monitoring instrument may also include a recording device, such as a magnetic tape recorder, or a digital display for providing a visual blood pressure indication.

In operation, the motor is energized to inflate the cuff while the pressure in the cuff is monitored by the pressure transducer. When the cuff pressure reaches a predetermined value, the processor periodically actuates an air valve to incrementally bleed air from the cuff thereby reducing the cuff pressure. At each cuff pressure value, the transducer(s) measure the cuff pressure and detect Korotkoff sounds or oscillometric pulses. The processor, using a rather complex algorithm, then determines the blood pressure from a table of cuff pressures and data indicating whether Korotkoff sounds or oscillometric pulses are detected at each cuff pressure. The blood pressure is then either recorded or displayed.

The conventional blood pressure monitors described above are effective in allowing the blood pressure of a patient to be accurately and easily measured and either displayed or recorded. However, it suffers from limitations stemming from the manner in which the motor driving the air pump is operated and/or controlled. In order to prevent the cuff pressure from exceeding the target value (which, in extreme instances, could be dangerous), the rate at which the blood pressure cuff must be limited. An excessive pump speed can also generate a great deal of noise and is thus generally undesirable in a hospital environment. Conversely, a very slow inflation rate may unduly increase the duration during which blood flow through the patient's arm is occluded and it needlessly prolongs the time required to make a blood pressure measurement.

While inflation rate can be adequately controlled under some conditions, the time required to inflate blood pressure cuffs will vary with different sizes of cuffs since the rate of air flow during inflation is substantially constant. The time required to inflate the cuff will also be affected by variations in the voltage applied to the motor driving the air pump. The optimum air flow rate will vary according to the size of the cuff. Larger cuffs, used by adults, require a faster flow rate for a given inflation period while smaller, neonatal cuffs must be inflated at a slower flow rate to achieve the same inflation period. The optimum use of the same measuring instrument with both adult and neonatal blood pressure cuffs thus requires that the flow rate be controlled. However, conventional blood pressure monitors inflate blood pressure cuffs at the same flow rate regardless of their size.

As mentioned above, the duration of the inflation cycle for conventional blood pressure monitors is also affected by variations in the voltage of the power supplied to the motor. The problem inherent in motor drive voltage variations is particularly acute in blood pressure monitoring because many blood pressure monitors are designed for ambulatory use. As a result, they must be powered by batteries, and the voltage that the batteries supply to the motor will diminish greatly as the batteries become discharged during use. Conventional blood pressure monitors thus inflate blood pressure cuffs at reduced flow rates as their batteries become discharged thereby increasing the duration of the inflation cycle.

The manner in which conventional blood pressure monitors inflate their blood pressure cuffs may also give a patient the false impression that the monitor is not operating satisfactory. As the cuff pressure reaches the target value, the rotational speed of the air pump motor slows. Insofar as the motor and/or pump emit an audible sound having a frequency component that corresponds to the rotational velocity of the motor, the reduced speed of the motor as the target pressure is reached creates the perception that the motor is straining. While this apparent motor strain does not damage the motor, it does create the impression in the mind of the user that the motor driving the pump is not capable of providing adequate pressure. Also, excessive pump speeds tend to generate excessive noise which can be very undesirable in a hospital environment.

SUMMARY OF THE INVENTION

It is an object of the invention to provide a system for controlling the air pressure pump motor of a blood pressure monitor so that blood pressure cuffs having a variety of sizes can be inflated at the optimum rate.

It is another object of the invention to provide a system for controlling the air pressure pump motor of a blood pressure monitor so that the rate of inflation will remain constant as a battery powering the monitor is reduced during use.

It is another object of the invention to provide a system for controlling the air pressure pump motor of a blood pressure monitor so that the user will not have the impression that the motor has an inadequate capacity.

These and other objects of the present invention are provided by a blood pressure monitor including an air pump having an output port connected to a blood pressure cuff for delivering pressurized air to the cuff responsive to rotation of a pump shaft. The pump shaft is driven by an electric motor that applies a rotational torque to the shaft that is a function of the voltage of electricity supplied to the motor. A pressure transducer generates a signal indicative of the air pressure in the blood pressure cuff, while the voltage applied to the motor is controlled by an adjustable power supply. A control circuit receiving the output of the pressure transducer compares the rate of cuff inflation to a desired rate of inflation. The control circuit then controls the adjustable power supply either to adjust the voltage applied to the motor to increase its rotational velocity if the inflation rate is less than the desired inflation rate or to decrease its rotational velocity if the inflation rate is greater than the desired inflation rate. The adjustable power supply preferable includes a switch connected in series with the motor and a relatively constant supply voltage so that the magnitude of the voltage applied to the motor is a function of the duty cycle of the closed condition of the switch. The switch can be controlled by a comparator that generates a square wave having a duty cycle that is a function of a comparison of the voltages applied to its two inputs. One input of the comparator is a feedback signal indicative of the voltage applied to the motor, while the other input of the comparator is a control signal indicative of a voltage that can be applied to the motor to cause the rate of inflation of the blood pressure cuff to equal the desired rate of cuff inflation. The control signal may be a pulse-width modulated square wave signal that is low-pass filtered to convert the square wave signal into a voltage that is proportional to the duty cycle of the square wave signal. The initial voltage applied to the motor is preferably equal to one-half the sum of the initial voltage applied to the motor during the previous inflation of the blood pressure cuff and the final voltage applied to the motor during the previous inflation of the blood pressure cuff. The initial voltage may also be adjusted as a function of the desired inflation time of the blood pressure cuff. The desired rate of inflation is preferably calculated by dividing the target pressure by a desired pump operating time. The rate of cuff inflation can then be compared to a desired rate of inflation by multiplying the desired rate of inflation by the time elapsed since starting the inflation of the blood pressure cuff to obtain a desired current pressure. The desired current pressure can then be compared to the actual current pressure as indicated by the pressure transducer.

BEST MODE FOR CARRYING OUT THE INVENTION

Figure 1:
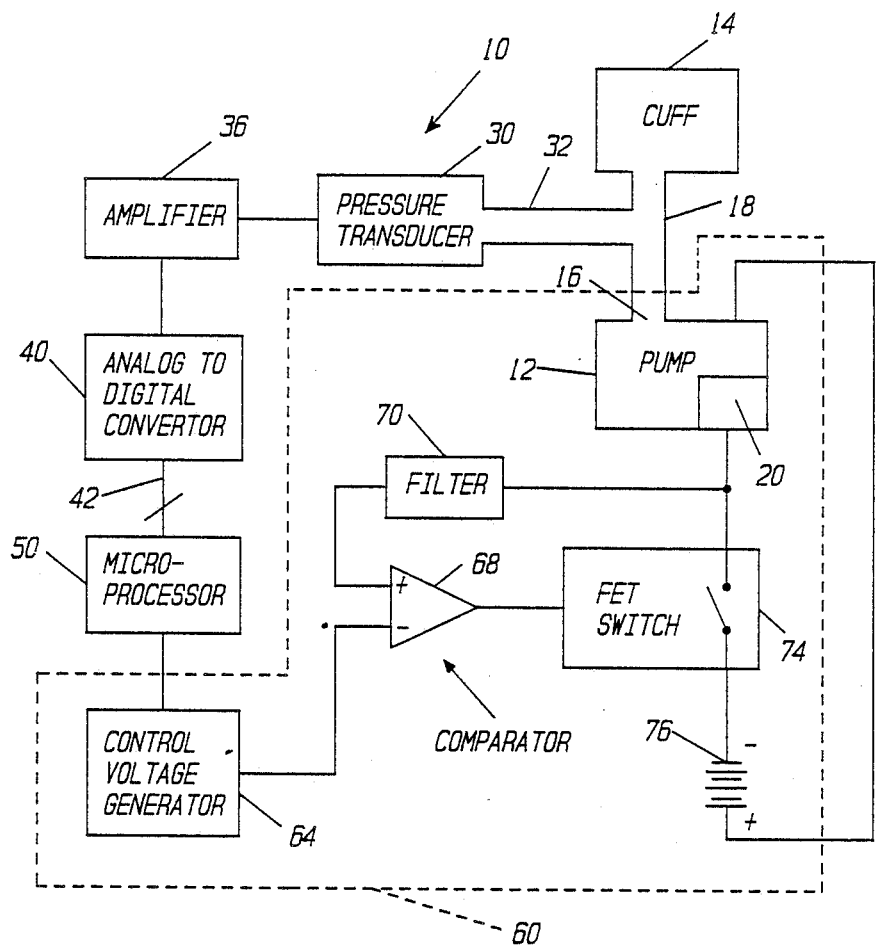
FIG. 1 is a block diagram of one embodiment of a system for controlling the rotational velocity of a motor driving a blood pressure cuff inflation motor.

The inventive inflation rate control system 10, as illustrated in FIG. 1, is adapted for use with a blood pressure monitor having a conventional air pump 12 and a blood pressure cuff 14 connected to the output port 16 of the pump 12 through a tube 18. As is well known in the art, the pump 12 includes an internal motor 20 driving an internal pumping mechanism through a rotary shaft (not shown). The volume and pressure of the air delivered to the air pressure port 16 is a function of the rotational velocity and torque of the motor 20. The air pump 12 may consist of a diaphragm pump driven by a DC motor.

The air pressure in the blood pressure cuff 14 is measured by a conventional pressure transducer 30 which is coupled to the cuff 14 through a tube 32. The pressure transducer 30 may be, for example, a pressure sensitive bridge circuit. The pressure transducer 30 generates an output signal indicative of the cuff pressure which is applied to an amplifier 36 of conventional design. The magnitude of the voltage at the output of the amplifier 36 is thus proportional to the air pressure in the blood pressure cuff 14.

The output of the amplifier 36 is applied to a conventional analog to digital converter 40 which generates a digital word on bus 42 indicative of the pressure in the blood pressure cuff 14. The digital cuff pressure indication is periodically sampled by a conventional microprocessor 50 operating in accordance with a program of instructions, as explained below. The microprocessor 50 can be a separate microprocessor dedicated to the operation of the inflation control circuit. Alternatively, the microprocessor 50 can be the same microprocessor that is used to control other subsystems in a blood pressure monitor.

As is well known in the art, the microprocessor 50 includes a number of output ports, one of which is connected to a pump motor control circuit 60. The pump motor control circuit includes a voltage control generator 64 receiving a control voltage from the microprocessor 50 in the form of a pulse-width modulated square wave. The control voltage generator 64 generates an analog voltage at its output that is proportional to the duty cycle of the received square wave. The analog voltage from the control voltage generator is applied to the negative input of a conventional comparator 68 which may be a commonly available operational amplifier or voltage comparator. The positive input of the comparator receives the output of a low-pass filter 70 which, in turn, is connected to the input to the pump motor 20. In steady state operation, the low-pass filtered voltage from the pump motor 20 that is applied to the positive input of the comparator 68 is approximately equal to the analog voltage output by the control voltage generator 64. In this mode, the comparator 68 oscillates between two states thereby generating a square wave at its output. However the pulse-width or duty cycle of the square wave varies depending upon the polarity of the comparison at the input to the comparator 68. When the signal applied to positive input of the comparator 68 is larger than the signal applied to the negative input of the comparator 68, the duty cycle of the square wave generated by the comparator 68 increases. Conversely, when the voltage applied to the negative input of the comparator 68 is greater than the voltage applied to the positive input of the comparator 68, the duty cycle of the square wave generated by the comparator 68 decreases.

The square wave output by the comparator 68 is applied to a conventional field affect transistor 74 operating as a switch. The switch 74 is connected in series between the negative terminal of a battery 76 and the motor 20. Thus, the amount of current flowing through the motor 20 is determined by the closed condition duty cycle of the switch 74.

In operation, as the voltage applied to the pump 20 becomes less negative, (i.e. more positive), the polarity of the comparison at the inputs to the comparator 68 becomes more positive thereby increasing the duty cycle of the square wave output by the comparator 68. This increased duty cycle increases the closed condition duty cycle of the switch 74 thereby puling the input to the pump 20 to the negative terminal of the battery 76 for a greater percentage of time. As a result, the average voltage applied to the pump 20 becomes more negative (i.e. less positive) until the duty cycle of a square wave generated by the comparator 68 reaches a steady state value.

As explained in greater detail below, during the inflation of the cuff 14, the microprocessor 50 compares the actual cuff pressure, as indicated by the pressure transducer 30, with a desired cuff pressure. The microprocessor 50 then adjusts the duty cycle of the square wave applied to the control voltage generator 64 to alter the voltage applied to the pump 20 thereby either increasing or decreasing the rate of cuff inflation 14 toward the desired inflation rate.

Figure 2:
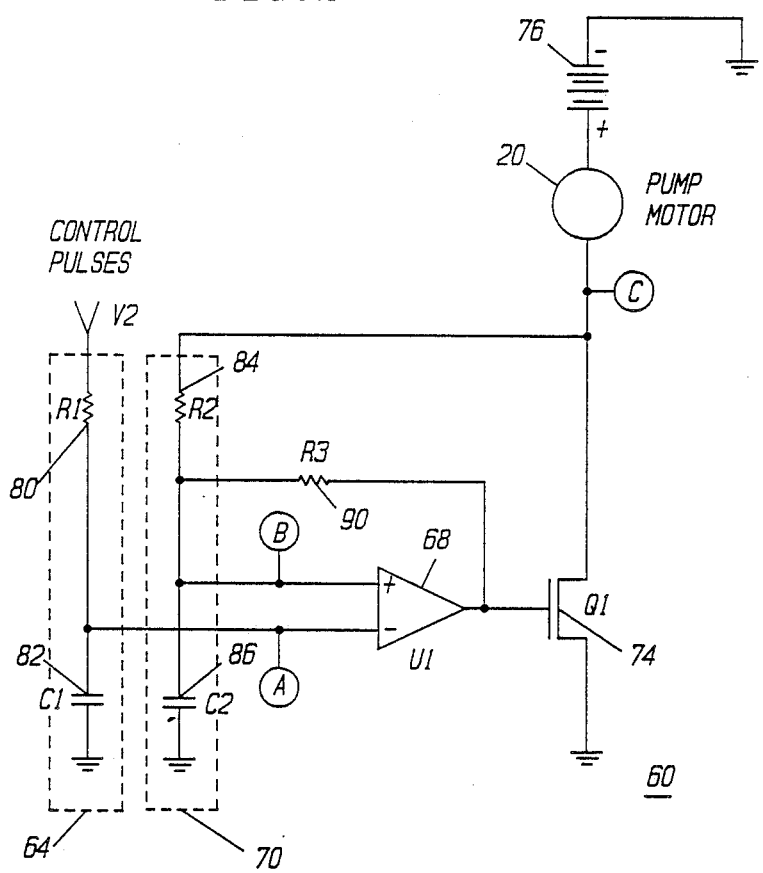
FIG. 2 is a schematic of a control circuit for controlling the rotational velocity of a motor in response to a control signal.
Figure 3:
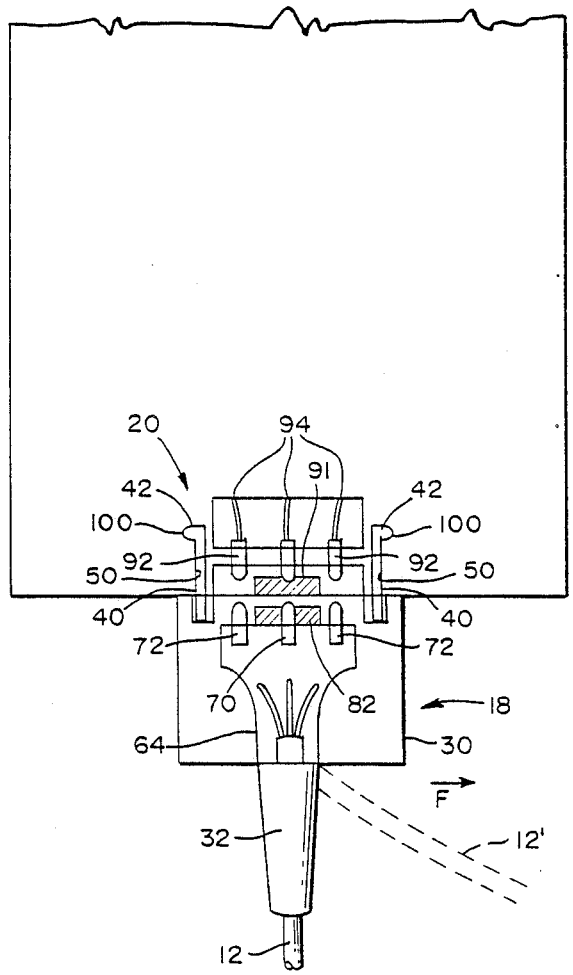

The inflation rate control circuit is illustrated in greater detail in FIG. 2. The control voltage generator 64 receiving the square wave from the microprocessor 50 (FIG. 1) consists of a resistor-capacitor low-pass filter formed by resistor 80 and capacitor 82. The voltage output by the control voltage generator 64 is thus a DC value that is equal to the logic "0" voltage plus the product of the duty cycle of the square wave and the difference between the magnitudes of the logic "1" voltage and the logic "0" voltage. The filter 70 connected to the input to the pump 20 is also an R-C low-pass filter formed by resistor 84 and capacitor 86. The voltage generated at the junction between the resistor 84 and the capacitor 86 is equal to $V_b \times (1-DC)$, where $V_b$ is the battery voltage and DC is the duty cycle of the signal applied to the pump 20.

As mentioned above, under steady state conditions, the voltages applied to both inputs of the comparator 68 are approximately equal. Under these circumstances, a positive feedback resistor 90 connected between the output and positive input of the comparator 68 causes the comparator 68 to oscillate. The output of the comparator 68 is thus a square wave having a duty cycle that is determined by the polarity of the voltages applied to its inputs. The output of the comparator 68 is connected to the gate of a conventional field effect transistor 74, as explained above.

In operation, the microprocessor 50 outputs a high logic level thereby maintaining the switch 74 in the off condition in order to allow the voltage applied to the positive input of the comparator 68 to have the same high value. When inflation of the blood pressure cuff 14 is to begin, the microprocessor 50 outputs a square wave having a duty cycle indicative of the pump voltage that is expected to produce the desired inflation rate. The reduction in duty cycle from 100% causes the voltage at the negative input of the comparator 68 to be substantially lower than the voltage applied to the positive input of the comparator 68. As a result, transistor 74 turns on thereby drawing current through the pump motor 20 and reducing the voltage applied to the positive input of the comparator 68. When the voltage applied to the positive input of the comparator 68 reaches the control voltage output by the control voltage generator 64, the transistor 74 turns off. The comparator 68 then enters an oscillatory mode at which the voltage applied to the pump motor 20 is substantially equal to the control voltage from the control voltage generator 64 by virtue of variations in the closed condition duty cycle of the FET switch 74.

The operation of the inflation rate control system illustrated in FIG. 1 can best be explained with reference to the following pseudo code:

| Initial Motor Voltage Calculation |
| --- |
| IF INITIAL TARGET REACHED LAST TIME |
| THEN |
| TEMP1 = LAST PUMP UP TIME − CURRENT DESIRED PUMP TIME |
| TEMP2 = LAST STARTING VOLTAGE + LAST ENDING VOLTAGE |
| STARTING VOLTAGE = (TEMP1 + TEMP2)/2 |
| ELSE |
| IF LAST READING ENDED VIA CANCEL DURING FIRST PUMP |
| OR LAST READING ENDED VIA OPEN HOSE ABORT |
| THEN |
| STARTING MOTOR VOLTAGE: = LAST STARTING MOTOR VOLTAGE |
| ELSE |
| IF LAST READING ENDED VIA A LOOSE CUFF ABORT |
| THEN |
| STARTING MOTOR VOLTAGE: = LAST ENDING MOTOR VOLTAGE |
| ELSE |
| IF LAST READING ENDED VIA KINKED HOSE ABORT |
| THEN |
| IF LAST STARTING VOLTAGE IS LESS THAN DEFAULT STARTING VOLTAGE |
| THEN |
| STARTING MOTOR VOLTAGE: = LAST STARTING MOTOR VOLTAGE |
| ELSE |
| STARTING MOTOR VOLTAGE: = DEFAULT MOTOR VOLTAGE |
| END IF |
| ELSE |
| STARTING MOTOR VOLTAGE: = LAST STARTING MOTOR VOLTAGE |
| END IF |
| END IF |

| Inflation Rate Correction Logic |
| --- |
| IF PUMP RUNNING AND INITIAL TARGET NOT YET REACHED |
| THEN |
| IF BEEP DESIRED |
| THEN |
| DESIRED PUMP TIME: = 15 SEC |
| ELSE |
| DESIRED PUMP TIME: = 20 SEC |
| END IF |
| DESIRED INFLATION RATE: = TARGET/DESIRED PUMP TIME |
| DESIRED CURRENT PRESSURE: = ELAPSED TIME + DESIRED INFLATION RATE |
| IF DESIRED CURRENT PRESSURE GREATER THAN TARGET PRESSURE |
| THEN |
| DESIRED CURRENT PRESSURE: = TARGET PRESSURE |
| END IF |
| IF ELAPSED TIME LESS THAN 6 SEC |

| Inflation Rate Correction Logic |
| --- |
| -continued |
| THEN
IF CURRENT PRESSURE GREATER THAN
(DESIRED CURRENT PRESSURE + 5)
THEN
MOTOR SPEED CONTROL BYTE: = MOTOR
SPEED CONTROL BYTE − 8
IF MOTOR SPEED CONTROL BYTE LESS
THAN MINIMUM
THEN
MOTOR SPEED CONTROL BYTE: =
MINIMUM
END IF
END IF
ELSE
SPEED UP GUARD: = 50 − ELAPSED SECONDS
IF SPEED UP GUARD LESS THAN 30
THEN
SPEED UP GUARD: = 30
END IF
IF CURRENT PRESSURE LESS THAN (DESIRED
CURRENT PRESSURE − SPEED UP GUARD)
THEN
MOTOR SPEED CONTROL BYTE: = MOTOR
SPEED CONTROL BYTE + 1
END IF
IF MOTOR SPEED CONTROL BYTE MAXIMUM
THEN
MOTOR SPEED CONTROL BYTE: =
MAXIMUM
END IF
END IF
END IF |

| Stall Control |
| --- |
| IF TOTAL PUMP ON TIME THIS MEASUREMENT
GREATER THAN 12 SECONDS
AND TIME SINCE LAST PUMP START GREATER THAN
2 SECONDS
THEN
IF BEEP DESIRED
THEN
DESIRED PUMP TIME: = 15 SEC
ELSE
DESIRED PUMP TIME: = 20 SEC
END IF
DESIRED INFLATION RATE: = TARGET/
DESIRED PUMP TIME
IF PRESSURE CHANGE OVER LAST SECOND LESS
THAN (DESIRED INFLATION RATE/2)
THEN
MOTOR SPEED CONTROL BYTE: = MOTOR
SPEED CONTROL BYTE + 5
IF MOTOR SPEED CONTROL BYTE GREATER
THAN MAXIMUM
THEN
MOTOR SPEED CONTROL BYTE: =
MAXIMUM
END IF
END IF
END IF |

The pseudo code illustrated above allows one skilled in the art to readily program various commercially available microprocessors to operate in accordance with the following description. The initial motor voltage at the start of an inflation cycle is first calculated. If the cuff 14 was previously inflated, the program sets the starting voltage to the sum of the voltage applied to the pump motor 20 at the start of the previous inflation cycle and the voltage at the end of the previous inflation cycle. This starting voltage is adjusted by a comparison of the time to pump the blood pressure cuff 14 to a target pressure with the desired time to inflate the cuff 14 to a target pressure in the current inflation cycle. A shorter pump time will, of course, require a larger voltage applied to the motor 20 in order to achieve the target pressure within the shorter period of time. If an inflation cycle for the blood pressure cuff 14 had previously started but, for some reason, was not completed, the starting motor voltage is set to the previous starting motor voltage. However, if the previous inflation cycle ended because the blood pressure cuff was loose, the starting voltage is set to the motor voltage at the end of the previous inflation cycle. If none of the foregoing conditions can be met, the starting voltage is set to a default motor voltage.

Once the initial motor voltage has been calculated, the motor voltage is adjusted depending upon the deviation of the actual inflation rate from a desired inflation rate. The desired pumping time is set for either 15 or 20 seconds and a desired inflation rate is then calculated as the ratio of the target cuff pressure to the desired pump time. The desired cuff pressure (i.e., current pressure) is then calculated at any point in time by multiplying the elapsed time since the start of the inflation cycle by the desired inflation rate. If the desired current pressure is greater than the target pressure, then the desired current pressure is reduced to the target pressure.

If the elapsed time from the start of the inflation cycle is less than 6 seconds, the microprocessor 50 determines if the current pressure is greater than the desired current pressure by a magnitude of 5. If so, the duty cycle of the square wave generated by the microprocesor 50 is reduced by an arbitrary value of 8. However, if the motor control signal calculated as stated above is less than a minimum value, then the control signal is set to the minimum value. If the current pressure is less than the sum of the desired current pressure and 5, then the voltage applied to the motor 20 must be increased to cause the pump 12 to operate at a higher speed. If the current pressure is less than a desired current pressure less a "speed-up guard" value (which initially starts at 50 and is decrement by the elapsed seconds), then the motor speed control duty cycle is increased by an arbitrary value of one. However, if the motor speed control duty cycle is greater than a predetermined maximum value, then the motor speed control duty cycle is set to the maximum value.

It is possible that the motor 20 driving the internal pump can become stalled, in which case rotation of the motor terminates. After the desired inflation rate is calculated as the ratio of the target pressure to the desired pump time, as explained above, the pressure change over the last second is compared to one-half the desired inflation rate. If the pressure change over the last second is less than one-half the desired inflation rate, then the motor speed control duty cycle is increased by an arbitrary value of 5, unless the motor speed control duty cycle so calculated is greater than a predetermined maximum value. In such case, the motor speed control duty cycle set is set to the maximum value. Thus, in the event of a motor stall condition, the duty cycle of the control signal is changed suddenly and drastically to increase the voltage supplied to the motor 20.

It is thus seen that the inflation rate control system can inflate a blood pressure cuff 14 at a controllable rate. The inflation rate automatically compensates for variations in the size of the blood pressure cuff 14 as well as for variations in the battery voltage 76, since the inflation rate is controlled solely by the duty cycle of the signal generated by the microprocessor 50.

I claim:

1. A blood pressure monitor comprising:
    an air pump having an output port and a rotatable shaft, said air pump delivering pressurized air to said output port responsive to rotation of said shaft;
    a blood pressure cuff connected to the output port of said air pump through a tube;
    an electric motor coupled to the rotatable shaft of said air pump, the rotational torque of said motor being a function of the voltage of electricity supplied to said motor;
    a pressure transducer generating a signal indicative of the air pressure in said blood pressure cuff;
    control circuit means receiving the output of said pressure transducer, said control circuit means calculating the rate of inflation of said blood pressure cuff over a predetermined period, comparing said rate of cuff inflation to a desired rate of inflation and generatign a control signal to adjust the voltage applied to said motor to increase its rotational velocity if the inflation rate is less than desired inflation rate and to decrease its rotational velocity if the inflation rate is greater than the desired inflation rate;
    a switch connected in series with said motor and a relatively constant supply voltage so that the magnitude of the voltage applied to said motor is a function of the duty cycle of the closed condition of said switch;
    comparator means having a pair of inputs and an output connected to and controlling the operation of said switch, said comparator means generating a square wave having a duty cycle that is a function of a comparison of the voltages applied to the two inputs of said comparator means;
    feedback means applying a voltage to one input of said comparator means that is indicative of the voltage applied to said motor; and
    command voltage generator means applying a command voltage to the other input of said comparator means responsive to said control signal, said command voltage being indicative of a voltage that, when applied to said motor, causes the rate of inflation of said blood pressure cuff to equal said desired rate of cuff inflation.

2. The blood pressure monitor of claim 1 wherein said control signal is a pulse-width modulated square wave signal, and wherein said command voltage generator means comprises a low-pass filter for converting said square wave signal into a voltage for use as said command voltage that is proportional to the duty cycle of said square wave signal.

3. A blood pressure monitor comprising:
    an air pump having an output port and a rotatable shaft, said air pump delivering pressurized air to said output port responsive to rotation of said shaft;
    a blood pressure cuff connected to the output port of said air pump through a tube;
    an electric motor coupled to the rotatable shaft of said air pump, the rotational torque of said motor being a function of the voltage of electricity supplied to said motor;
    a pressure transducer generating a signal indicative of the air pressure in said blood pressure cuff;
    control circuit means receiving the output of said pressure transducer, said control circuit means calculating the rate of inflation of said blood pressure cuff over a predetermined period, comparing said rate of cuff inflation to a desired rate of inflation and generating a control signal to adjust the voltage applied to said motor to increase its rotational velocity if the inflation rate is less than desired inflation rate and to decrease its rotational velocity if the inflation rate is greater than the desired inflation rate, said control circuit means further calculating the initial voltage applied to said motor as equal to one-half the sum of the initial voltage applied to said motor during the previous inflation of said blood pressure cuff and the final voltage applied to said motor during the previous inflation of said blood pressure cuff.

4. The blood pressure monitor of claim 3 wherein said initial voltage is adjusted as a function of the desired inflation time of said blood pressure cuff.

5. A system for controlling the rotational velocity of a motor driving an air pump for inflating a blood pressure cuff, comprising:
    a switch connected in series with said motor and a relatively constant supply voltage so that the magnitude of the voltage applied to said motor is a function of the duty cycle of the closed condition of said switch;
    comparator means having a pair of inputs and an output connected to and controlling the operating of said switch, said comparator means generating a square wave having a duty cycle that is a function of a comparison of the voltages applied to the two inputs of said comparator means;
    feedback means applying a voltage to one input of said comparator means that is indicative of the voltage applied to said motor; and
    command voltage generator means applying a command voltage to the other input of said comparator means responsive to a control signal, said command voltage being indicative of a voltage that, when applied to said motor, causes the rate of inflation of said blood pressure cuff to equal said desired rate of cuff inflation; and control circuit means calculating the rate of inflation of said blood pressure cuff over a predetermined period, comparing said rate of cuff inflation to a desired rate of inflation and generating said control signal to adjust the voltage applied to said motor to increase its rotational velocity if the inflation rate is less than the desired inflation rate and to decrease its rotational velocity if the inflation rate is greater than the desired inflation rate.

6. The system of claim 5 wherein said control signal is a pulse-width modulated square wave signal, and wherein said command voltage generator means comprises a low-pass filter for converting said square wave signal into a voltage for use as said command voltage that is proportional to the duty cycle of said square wave signal.

7. A system for controlling the rotational velocity of a motor driving an air pump for inflating a blood pressure cuff, comprising:

adjustable power supply means for applying a voltage to said motor that is determined by a control signal; and control circuit means calculating the rate of inflation of said blood pressure cuff over a predetermined period, comparing said rate of cuff inflation to a desired rate of inflation and generating said control signal to adjust the voltage applied to said motor to increase its rotational velocity if the inflation rate is less than the desired inflation rate and to decrease its rotational velocity if the inflation rate is greater than the desired inflation rate, said control circuit means further calculating the initial voltage applied to said motor as equal to one-half of the sum of the initial voltage applied to said motor during the previous inflation of said blood pressure cuff and the final voltage applied to said motor during the previous inflation of said blood pressure cuff.

8. The system of claim 7 wherein said initial voltage is adjusted as a function of the desired inflation time of said blood pressure cuff.

9. A method of controlling the rotational velocity of a motor driving an air pump for inflating a blood pressure cuff, said method comprising:

calculating the rate of inflation of said blood pressure cuff over a predetermined period;

comparing said rate of cuff inflation to a desired rate of inflation;

selecting an initial voltage to apply to said motor, said initial voltage being equal to one-half of the sum of the initial voltage applied to said motor during the previous inflation of said blood pressure cuff and the final voltage applied to said motor during the previous inflation of said blood pressure cuff; and adjusting the voltage applied to said motor to increase its rotational velocity if the inflation rate is less than the desired inflation rate and to decrease its rotational velocity if the inflation rate is greater than the desired inflation rate.

10. The method of claim 9 further including the step of adjusting the initial voltage applied to said motor as a function of the desired inflation time of said blood pressure cuff.

* * * * *

UNITED STATES PATENT AND TRADEMARK OFFICE
CERTIFICATE OF CORRECTION

PATENT NO. : 4,969,466
DATED : November 13, 1990
INVENTOR(S) : James R. Brooks

It is certified that error appears in the above-identified patent and that said Letters Patent is hereby corrected as shown below:

In claim 1, column 9, line 50, please delete "generatign" and substitute therefor --generating--.

Signed and Sealed this

Seventh Day of April, 1992

Attest:

HARRY F. MANBECK, JR.

*Attesting Officer*      *Commissioner of Patents and Trademarks*